United States Patent [19]

Takahashi et al.

[11] 4,239,928

[45] Dec. 16, 1980

[54] PROCESS FOR PREPARING ALKYL-SUBSTITUTED AROMATIC COMPOUNDS

[75] Inventors: Kunimasa Takahashi; Takashi Yokoi, both of Ami, Japan

[73] Assignee: Mitsubishi Petrochemical Co. Ltd., Tokyo, Japan

[21] Appl. No.: 11,949

[22] Filed: Feb. 13, 1979

[30] Foreign Application Priority Data

Feb. 15, 1978 [JP] Japan ................... 53-15330

[51] Int. Cl.$^2$ .................. C07C 15/02; C07C 5/36
[52] U.S. Cl. ............................ 585/431
[58] Field of Search ................ 585/431, 440

[56] References Cited

U.S. PATENT DOCUMENTS

| | | | |
|---|---|---|---|
| 3,903,185 | 9/1975 | Vogel et al. | 585/431 |
| 4,029,715 | 6/1977 | Rieve et al. | 585/431 |
| 4,048,243 | 9/1977 | Ruckelshauss | 585/431 |

*Primary Examiner*—Veronica O'Keefe
*Attorney, Agent, or Firm*—Sherman & Shalloway

[57] ABSTRACT

A process for preparing corresponding alkyl-substituted aromatic compounds by the gas phase catalytic dehydrogenation of vinylcycloalkenes in the presence of a dehydrogenation catalyst supported on a carrier, said catalytic dehydrogenation being carried out (i) in the presence of a dehydrogenation catalyst in which at least one of elements belonging to periods 5 and 6 in the group VIII of the periodic table selected from the group consisting of palladium, rhodium, platinum, iridium and ruthenium is supported on active carbon (ii) by introducing steam into the reaction system, (iii) but without introducing hydrogen into the reaction system, (iv) at conditions of temperatures ranging from 300° C. to less than 350° C. and pressure less than 2.5 atm (absolute pressure), wherein a liquid hourly space velocity (LHSV) is set at about 5 hr$^{-1}$ or less when the catalytic dehydrogenation is effected in the presence of said catalyst in which palladium alone is supported on active carbon.

10 Claims, No Drawings

PROCESS FOR PREPARING ALKYL-SUBSTITUTED AROMATIC COMPOUNDS

The instant invention relates to a low temperature-low pressure process for production of alkyl-substituted aromatic compounds suited for the practice on an industrial scale capable of holding down the occurrence of unfavorable side-reactions to advantage and capable of preparing the corresponding alkyl-substituted aromatic compounds, such as ethylbenzene, by the gas phase catalytic dehydrogenation reaction of vinylcycloalkenes, such as 4-vinylcyclohexene-1, stably over a prolonged period of time with excellent catalyst activity and high selectivity.

More particularly, the instant invention is concerned with a process for preparing corresponding alkyl-substituted aromatic compounds by the gas phase catalytic dehydrogenation of vinylcycloalkenes in the presence of a dehydrogenation catalyst supported on a carrier, said catalytic dehydrogenation being carried out (i) in the presence of a dehydrogenation catalyst in which at least one of elements belonging to periods 5 and 6 in the group VIII of the periodic table selected from the group consisting of palladium, rhodium, platinum, iridium and ruthenium is supported on active carbon (ii) by introducing steam into the reaction system, (iii) but without introducing hydrogen into the reaction system, (iv) at conditions of temperatures ranging from 300° C. to less than 350° C. and pressures less than 2.5 atm (absolute pressure), wherein a liquid hourly space velocity (LHSV) is set at about 5 $hr^{-1}$ or less when the catalytic dehydrogenation is effected in the presence of said catalyst in which palladium alone is supported on active carbon.

Heretofore, some proposals are known of preparation of corresponding alkyl-substituted aromatic compounds by the gas phase catalytic dehydrogenation of vinylcycloalkenes in the presence of a dehydrogenation catalyst, including the case for carrier-supported dehydrogenation catalyst.

A proposal is made in the U.S. Pat. No. 3,903,185 (published Sept. 2, 1975), for instance, of a process for production of corresponding alkyl-substituted aromatic compounds, such as ethylbenzene, by the gas phase catalytic dehydrogenation of $C_8$-cycloolefins, such as 4-vinylcyclohexene-1, in the presence, as catalyst, of metals and/or metal oxides of sub-groups VI, VII and VIII of the periodic table, including metals belonging to the platinum group. In this proposal, as suitable and preferred catalyst are cited platinum catalysts, or catalysts containing platinum and rhenium or cobalt and molybdenum oxide. Catalyst supported on suitable porous material is described as advantageous and silica gel, kieselguhr, asbestos, graphite and active charcoal are cited. Emphasis is placed upon the fact that aluminum oxides and $\gamma$-aluminum oxide, in particular, has proved to be a particularly suitable support.

In fact, it is a $\gamma$-alumina carrier alone that is used throughout the whole examples in this proposal, and use is made of $CoO-MoO_3-\gamma$-alumina catalyst and Pt-Re-$\gamma$-alumina catalyst and Pt-$\gamma$-alumina catalyst, but there is no disclosing of specific example in which active carbon is used as a carrier.

Further, this proposal teaches that hydrogen pressure should be set at 2.5–30 atm, preferably 5–12 atm, to avoid excess carbon deposition on the catalyst and make the thermodynamic equilibrium lying insofar as possible to the side of the end product ethylbenzene, and recommends to carry out the reaction at pressure conditions of 2.5 to 30 atm (absolute pressure) and under temperature conditions of 350° C. to 450° C. and 380° C. to 420° C., in particular. These pressure conditions and temperature conditions are set forth as indispensable requirements in the scope of the claim for the patent. In all of the examples the reaction is carried out by introducing into the catalytic reaction system 2 $Nm^3$ or 6 $Nm^3$ of hydrogen gas per kg of starting 4-vinylcyclohexene-1 along with the 4-vinylcyclohexene-1 for the purpose of meeting such requirements.

As mentioned above, in this proposal active carbon could be used, but it is recommended that the $\gamma$-alumina carrier should optimally be used, and it is also recommended that the catalytic reaction under pressure should be carried out at pressure and temperature conditions of 2.5 to 30 atm, preferably 5 to 12 atm, and 350° C. to 450° C., preferably 380° C. to 420° C. while introducing hydrogen gas in a substantial amount into the catalytic reaction system. The process of this proposal, however, requires the addition of a compression system for the hydrogen gas introduced into the reaction system and further optionally hydrogen gas separation and purification systems. This additional apparatus is expensive and results in operational difficulties. This proposal teaches the necessity of carrying out the reaction while introducing hydrogen gas in a substantial amount into the reaction system at relatively high temperature and pressure conditions notwithstanding the apparatus requirements and operational difficulties for avoiding amounts of unfavorable by-products ethylcyclohexane and ethylcyclohexene formed from accumulating to significantly detrimental levels or for oxidizing excess carbon deposition on the catalyst.

As an attempt to improve upon and avoid the above mentioned drawbacks relating to the introduction of hydrogen gas of the proposal of U.S. Pat. No. 3,903,185, U.S. Pat. No. 4,029,715 (published June 14, 1977) teaches that the reaction should be carried out at pressure conditions of about 0.4 atm to about 8 atm and at high temperature conditions of about 400° C. to about 450° C. by introducing a reactant stream substantially free from hydrogen comprising a major amount of an inert gas selected from the group consisting of nitrogen, steam, carbon dioxide, argon and mixtures thereof and a minor amount of $C_8$-cycloolefin into the catalytic reaction zone having a catalyst bed of $CoO-MoO_3-\gamma$-alumina catalyst carrying about 0.9 to about 3% $K_2O$. This proposal involves the using of a great deal of dilute inert gas, which in turn, on the occasion of separation and purification of the end product, entails such trouble in the operation and such disadvantage in the apparatus caused by the handling of the product stream less in the content of the end product, and it is inevitably high in costs.

The instant inventors carried out research directed to providing an improved process with a combination of various improvements which were hardly compatible in these respective proposals by overcoming various demerits with the heretofore-made proposals.

As a consequence, by effecting the gas phase catalytic dehydrogenation reaction at conditions which meet the requirements (i)–(iv) of the instant invention, wherein a liquid hourly space velocity (LHSV) is set at about 5 $hr^{-1}$ when the reaction is conducted in the presence, as the catalyst set froth in the requirement (i), of a catalyst in which palladium alone is supported on active carbon, various demerits of the heretofore-made proposals could be overcome to while at the same time obtaining the advantage of being able to use a comparatively low temperature-low pressure system which is more advantageous in the operation as well as in the apparatus as compared with the conventional proposals. In addition in the present invention the occurrence of disadvantageous side-reactions could be held down with more ease, and it was found that corresponding alkyl-substituted aromatic compounds could be prepared by the gas phase catalytic dehydrogenation reaction of vinylcycloalkenes stably over a prolonged period of time with excellent catalytic activity and high selectivity as compared with those in the conventional proposals.

This was really surprising in terms of the fact that the former of the said proposals describes as indispensable the introduction of hydrogen, recommends to use γ-alumina, in particular, as the best-suited carrier and further recommends to employ a comparatively high temperature-high pressure reaction preferably at 380° to 420° C. and 5 to 12 atm, as well as the fact that the latter proposal recommends a process describing as indispensable the using of the γ-alumina supported cobaltmolybdenum type catalyst without introducing hydrogen and the using of a great deal of diluent inert gas and a high temperature reaction at 400° C. or more for the purpose of overcoming the demerits with the former proposal.

Furthermore, it was found that according to the instant invention, the reaction could be carried out to marked advantage in the industrial operation as well as in the apparatus, such as to be advantageously feasible at temperatures less than 350° C., such as in the vicinity of about 330° C. and further to be advantageously feasible even at less than 2.5 atm (absolute pressure), such as at atmospheric pressure conditions.

As the reaction can be conducted at an increased LHSV of vinylcycloalkenes in the order of about 8 with 100% conversion of vinylcycloalkenes and above 99% selectivity of corresponding alkylaromatics, the catalyst cost included in the product price can be remarkably reduced even in the case where production load of the process is fluctuated in low level. Thus, it was found that it could be effected on an industrial scale to marked advantage.

Therefore, the purpose of the instant invention is to provide an improved process capable of preparing corresponding alkyl-substituted aromatic compounds commercially to marked advantage by the gas phase catalytic dehydrogenation reaction of vinylcycloalkenes.

The said purpose of the instant invention and many other purposes and merits will be made more clear from descriptions given below.

According to the instant invention, in the preparation of corresponding alkyl-substituted aromatic compounds by the gas phase catalytic dehydrogenation of vinylcycloalkenes in the presence of a carrier-supported dehydrogenation catalyst, the catalytic dehydrogenation is effected under such conditions as to meet the requirements (i) to (iv), wherein, the LHSV is set at about 5 hr$^{-1}$ or less when the catalytic dehydrogenation is carried out in the presence, as the catalyst set forth in the requirement (i), of a catalyst in which palladium alone is supported on active carbon.

Besides the catalyst in which one of elements belonging to periods 5 and 6 in the group VIII of the periodic table selected from the group consisting of palladium, rhodium, platinum, iridium and ruthenium, such as palladium-carbon, rhodium-carbon, platinum-carbon, iridium-carbon, ruthenium-carbon and so on, use can be made of a catalyst in which a plurality of the said elements are supported on active carbon, which is preferred in the respect that it is suited for the employment of high LHSV conditions and that it is low in costs, and the like.

In a preferred embodiment the dehydrogenation catalyst of the requirement (i) is a catalyst in which a major amount of palladium and a minor amount of at least one of elements selected from the group consisting of rhodium, platinum, iridium and ruthenium are supported on active carbon. On this occasion, the quantitative ratio of the main constituent palladium and the secondary constituent element (if the secondary constituent element is present in plurality, it is a total of those constituent elements) should, in an atomic ratio, be preferably 1:0.001 to 1:0.5, more preferably 1:0.005 to 1:0.3, and still more preferably in the order of 1:0.01 to 1:0.1.

The catalyst used in the process of the instant invention could readily be prepared by supporting a noble metal compound, such as illustrated above, on active carbon by supporting means known per se. The configuration of active carbon could be suitably chosen. For instance, it can take a particulate, columnar, hollow columnar, fragmental and other optional finely divided product form or molded product form. The supporting on the active carbon of the noble metal compound could be achieved by immersing active carbon in a solution of the noble metal compound or spraying active carbon with said solution, followed by drying by a suitable means for effecting reduction treatment. This could be done, for instance, by immersing particles of active carbon which are thoroughly wetted in advance with deionized water in an aqueous solution of palladium chloride in hydrochloric acid or an aqueous solution in which rhodium chloride or chloroplatinic acid is further dissolved, slowly evaporating and drying the liquid content over the water bath under water-jet pump pressure, further drying by means of air oven at a suitable temperature and time, such as about 110° C. for about 20 hours and packing the reaction tube, for instance, with a suitable amount of the dried substance to subject to hydrogen reduction treatment in a hydrogen stream at a temperature in the order of about 300° C. to about 400° C. for several hours.

As such noble metal compounds, besides the above-illustrated chlorides, other water-soluble compounds, such as nitrate, sulphate, bromide and so on, could be used, but it is preferred to use chlorides because of convenience and stabilized tractability. Reduction treatment could be effected by other treating means, such as hydrazine reduction, carbon monoxide reduction and so on, but hydrogen reduction treatment is preferred.

Amounts of elements selected from the group of elements belonging to periods 5 and 6 in the group VIII of the periodic table to support on the active carbon carrier could be suitably chosen, but these should be preferably about 0.1 to about 20 parts by weight, as element, based on 100 parts by weight of active carbon. More preferably it should be about 0.5 to about 10 parts by weight and still further preferably in the order of about 1 to about 5 parts by weight. Even in the case of making use of a major amount of palladium and a minor amount of at least one of elements selected from the group consisting of rhodium, platinum, iridium and ruthenium in combination according to the preferred embodiment, similar palladium amounts to that which was illustrated above could be cited, and the secondary constituent element could be better supported on this palladium in the quantitative ratio of the amount illustrated above.

According to the process of the instant invention the gas phase catalytic dehydrogenation reaction is effected (i) in the presence of the said catalyst (ii) by introducing steam into the reaction system, (iii) but without introducing hydrogen into the reaction system, (iv) at temperatures from 300° C. to less than 350° C. and pressures less than 2.5 atm.

The embodiment where 4-vinylcyclohexene-1 is used as starting vinylcycloalkene to prepare corresponding ethylbenzene is particularly preferred in the process of the instant invention. The process of the instant invention is usable even in the embodiment where from other vinylcycloalkenes, such as 3-vinylcyclohexene-1, 2-vinylcyclohexene-1 and so on, the corresponding alkyl-substituted aromatic compounds of these, such as ethylbenzene, are prepared.

The reaction is conducted under low pressure conditions of less than 2.5 atm (absolute pressure). In the process of the instant invention, it is not necessary to employ pressure conditions, in particular, and it could be carried out even under atmospheric pressure conditions, which is rather preferred. Employment low pressure conditions in the range of atmospheric pressure to 2 atm (absolute pressure) could be cited. In the process of the instant invention the reaction can be conducted at such low pressure conditions, which is very advantageous operationwise as well as apparatuswise. It is also possible to employ reduced pressure conditions, if desired. Further, the reaction is carried out at low temperature conditions of 300° C. to less than 350° C., preferably about 310° C. to about 340° C. The fact that excellent results could be obtained by the employment of such low temperature conditions as to be as low as possible, coupled with the low pressure conditions, leads to advantageous practice on an industrial scale of the catalytic dehydrogenation by the low temperature-low pressure system of the instant invention.

In the practice of the process of the instant invention the LHSV of starting vinylcycloalkene could be suitably selected, but it should preferably be about 0.1 to about 20 hr$^{-1}$, more preferably about 0.5 to about 10 hr$^{-1}$ and still more preferably about 1 to about 8 ml of liquid vinylcycloalkene/ml-catalyst/hr (about 1 to about 8 hr$^{-1}$). If palladium-carbon is chosen as the catalyst of the requirement (i), as already mentioned, LHSV conditions of about 5 hr$^{-1}$ or less are better selected.

The reaction is conducted while steam is introduced into the reaction system. It is common to introduce the steam along with starting vinylcycloalkene. On this occasion, proportions of steam to vinylcycloalkene are preferably about 20 moles of steam/mole of vinylcycloalkene, more preferably about 1 mole to about 10 moles, and still more preferably about 2 moles of about 5 moles of steam/mole of vinylcycloalkene. By using the end alkyl-substituted aromatic compound, such as ethylbenzene, formed together with the steam, steam and ethylbenzene can be utilized as dilute gas. On this occasion, proportions of alkyl-substituted aromatic compound, such as ethylbenzene, to starting vinylcycloalkene, such as 4-vinylcyclohexene-1 are 0 to 100, preferably about 1 to about 20, more preferably about 2 to about 10 moles of ethylbenzene/mole of 4-vinylcyclohexene-1.

Non-condensable dilute gas, such as nitrogen, carbon dioxide, methane, butene and so on, could be introduced into the reaction zone, if desired.

According to the process of the instant invention nearly as high conversion as 100 mole% could be achieved at all times for per-pass conversion of starting vinylcycloalkenes, such as 4-vinylcyclohexene-1. In the case of using palladium alone as the catalyst element, if the LHSV goes too high, selectivity to alkyl-substituted aromatic compounds, such as ethylbenzene, is lowered and there is a tendency of producing ethylcyclohexene as by-product. In such a case employment of too high a LHSV is better avoided, and about 5 hr$^{-1}$ or less could be used.

The preparation of ethylbenzene from 4-vinylcyclohexene-1, as representative example, together with comparative examples, will be illustrated by way of working examples with reference to several embodiments for the practice of the process of the instant invention.

In this connection, analyses and determinations of reaction products were all made by gas chromatography and the amount of hydrogen generated was measured and determined by means of wet gas meter.

The reaction product was identified in part by the gas chromatography-mass spectrometer system. Conversion and selectivity were all expressed by mole% according to definitions represented by following equations.

$$\text{Coversion of 4-vinylcyclohexene-1} = \frac{\text{fed 4-vinylcyclohexene-1} - \text{unconverted 4-vinylcyclohexene-1)}}{\text{fed 4-vinylcyclohexene-1}} \times 100$$

$$\text{Selectivity to ethylbenzene} = \frac{\text{ethylbenzene in product}}{\text{fed 4-vinylcyclohexene-1} - \text{unconverted 4-vinylcyclohexene-1}} \times 100$$

EXAMPLE 1

40 g (100 parts) of SHIRASAGI active carbon particles (8–32 mesh, made by Takeda Chemical Industries, Ltd.) were wetted with deionized water, and immersed in 50 ml of 0.59 N hydrochloric acid solution containing 1.33 g of PdCl$_2$ which corresponds to 0.8 g (2 parts) of metallic palladium. Evaporation of the composition to dryness was done over water bath held at 50° C. using rotary evaporator under water jet pump pressure. It was further dried at 110° C. for 20 hours in an air drying oven. Of the composition obtained a stainless steel reaction tube 15 mm in inner diameter was packed with 12.5 ml (4.49 g) and on top Raschig rings were packed 15 cm high in a layer as a preheating layer. The composition was reduced at 300° C. for 3 hours with hydrogen flow (=1.0 l/minute) and the system was thoroughly replaced with nitrogen. Catalyst obtained was designated as 2Pd-100C. The reaction was carried out respectively at 4-vinylcyclohexene-1: about 15 ml/hr, a molar ratio of steam/4-vinylcyclohexene-1: about 3.0 and reaction temperatures=310° C. and 330° C. Table 1 shows inspection results of catalyst performances 1 hour to 3 hours after the reaction was initiated at the respective temperatures along with reaction conditions.

Further, for the 4-vinylcyclohexene-1 a commercially available product was treated with a 1 N-NaOH solution, further cleansed with pure water, then distilled at 60° C. under reduced pressure and used.

Comparative Example 1 (in which hydrogen gas was introduced into the reaction system)

By using the catalyst of Example 1, hydrogen/4-vinylcyclohexene-1 was fed at the rate of about 10 moles/mole (about 93 moles of hydrogen kg-4-vinylcyclohexene-1). The reaction was conducted at the reaction temperature=310° C. under conditions of 4-vinylcyclohexene-1=about 15 ml/hr. Table 1 shows inspection results of catalyst performances 1 hour to 3 hours after the reaction was initiated. Results obtained by simultaneously passing through hydrogen and steam at 310° C. were listed together.

Comparative Example 2 (in which hydrogen gas was introduced into the reaction system)

Catalyst was prepared by following the same procedure as that of Example 1. Active carbon having been wetted in advance with deionizing water was immersed in 50 ml (containing 0.8 g of palladium) of a 0.59 N aqueous solution of palladium chloride in hydrochloric acid in the amount enough to support 2 parts by weight of metal palladium with regard to 100 parts by weight (40 g) of active carbon and a uniform aqueous solution of rhodium chloride in the amount corresponding to 0.01 atom of rhodium with regard to 1 atom of metal palladium, evaporated to dryness and dried. The same reaction tube as used in Example 1 was packed with 12.5 ml of the composition obtained. It was subjected to hydrogen treatment at the same conditions. Catalyst obtained was designated as 0.01Rh-2Pd-100C. The reaction was conducted at reaction temperature=310° C. under conditions of passing through hydrogen. Table 1 shows results obtained.

EXAMPLE 2

The reaction was conducted in the presence of 12.5 ml of 2Pd-100C obtained by following the same formulation procedure as in Example 1 at a LHSV of 5.8 and reaction temperature of 330° C. under conditions for copresence of steam. Table 1 shows results obtained together with reaction conditions.

EXAMPLE 3

The reaction was conducted in the presence of 12.5 ml of 0.01Pt-2Pd-100C obtained by following the same formulation procedure as in Comparative Example 2 under such conditions as shown in Table 1 at a LHSV set at 3.85. Table 1 shows results obtained. In this connection, for platinum chloroplatinic acid was dissolved in an aqueous solution of palladium chloride in hydrochloric acid and used.

EXAMPLE 4

The reaction was conducted in the presence of 12.5 ml of 0.01Rh-2Pd-100C obtained by following the same procedure as that of Comparative Example 2 at such conditions as shown in Table 1. Table 1 shows results obtained.

EXAMPLE 5

Table 1 shows performance test results in the case of using 12.5 ml of 1.95Rh-100C (corresponding to 2.02 parts by weight of palladium supported on 100 parts by weight of active carbon) obtained by following the same procedure as that of Example 1 by supporting 96.9 ml of aqueous $RhCl_3$ solution containing metal rhodium (0.39 g) (3.91 mmol Rh/100 ml) on 100 parts by weight (20 g) of active carbon.

EXAMPLE 6

Table 1 shows performance test results in the case of using 12.5 ml of 3.71Pt-100C (corresponding to 2.02 parts by weight of palladium supported on 100 parts by weight of active carbon) obtained by following the same procedure as that of Example 1 by supporting 195 ml of aqueous $H_2PtCl_6$ solution containing metal platinum (0.742 g) (1.954 mmole Pt/100 ml) on 100 parts by weight (20 g) of active carbon.

EXAMPLE 7

Table 1 shows results obtained when inspecting catalyst performances with 12.5 ml of 0.01Ir-2Pd-100C obtained by following the same procedure as that of Comparative Example 2. Iridium was supported on 20 g of active carbon by dissolving 0.0126 g of iridium tetrachloride into 25 ml (containing 0.4 g of palladium) of a 0.59 N aqueous solution of palladium chloride in hydrochloric acid.

COMPARATIVE EXAMPLE 3

300 g of $Co(NO_3)_2.6H_2O$ was dissolved in 150 ml of water and stirred by means of a mixer. An aqueous solution obtained by dissolving 250 g of $(NH_4)HCO_3$ into 1,250 ml of water was added thereto dropwise in 20 minutes. After aging for 10 minutes it was filtered at reduced pressure and further cleansed with 200 ml of pure water to filter at reduced pressure. 16.05 g of Co-precipitates (Co content 30.04%) so obtained and 20.31 g of ammonium molybdate were dissolved in a mixed solution of 60 ml concentrated aqueous ammonia and 60 ml pure water. 100 g of $\gamma$-$Al_2O_3$ (FUJIMI KENMAZAI CO., B-19, 1.5 mm$\phi$) was immersed, and excess moisture was removed over water bath held at 90° C. and it was further dried to dryness at 90° C. under water-jet pump pressure. The composition so obtained was further dried at 110° C. for 16 hours and salt decomposition was carried out at 500° C. for 5 hours in a muffle furnace. The composition obtained was designated as 5CoO-13.5$MoO_3$-81.5$\gamma$-$Al_2O_3$ (by weight%) which corresponded to the catalyst used in the U.S. Pat. No. 3,903,185 (Example 1).

The reaction tube was packed with 10 ml (7.58 g) of the composition obtained. It was reduced with hydrogen (1.0 l/min.) at 330° C. for 4 hours. After that, the reaction was conducted at 330° C. under such conditions as shown in Table 1. Table 1 shows results obtained.

COMPARATIVE EXAMPLE 4

Catalyst was prepared by following the same procedure as that of Comparative Example 3 by using 26.18 g of the Co-precipitates described in Comparative Example 3, 35.04 g of ammonium molybdate, 6.29 g of potassium carbonate and 100 g of $\gamma$-$Al_2O_3$ (B-19, 1.5 mm$\phi$). The composition obtained was designated as 3$K_2O$-7CoO-20$MoO_3$-70$\gamma$-$Al_2O_3$ (by weight%) which corresponded to the catalyst used in the U.S. Pat. No. 4,029,715 (Example 5). Catalyst was packed in the amount of 10 ml (8.78 g) and hydrogen reduction was effected at 330° C. for 4 hours. The reaction was conducted at the reaction temperature of 330° C. under such conditions as shown in Table 1. Table 1 shows results obtained.

TABLE 1

| Example No. | Catalyst | Reaction temperature (°C.) | LHSV (hr$^{-1}$) | STM/VCH (mole/mole) | H$_2$/VCH (mole/mole) | VCH Conversion (%) | Selectivity (%) EB | Selectivity (%) ECH |
|---|---|---|---|---|---|---|---|---|
| Ex. 1 | Pd-C | 310 | 1.19 | 3.17 | — | 99.9 | 98.1 | 1.3 |
| " | " | 330 | 1.20 | 3.06 | — | 99.9 | 98.7 | 0.9 |
| Comparative Example 1 | " | 310 | 1.18 | 3.11 | 10.2 | 100.0 | 89.8 | 10.1 |
| | " | 310 | 1.18 | — | 10.1 | 100.0 | 88.3 | 10.9 |
| Comparative Example 2 | Rh-Pd-C | 310 | 1.22 | — | 9.6 | 100.0 | 89.8 | 7.8 |
| Ex. 2 | Pd-C | 330 | 3.80 | 2.96 | — | 100.0 | 97.1 | 0.4 |
| Ex. 3 | Pt-Pd-C | 330 | 3.85 | 2.88 | — | 100.0 | 98.0 | 1.0 |
| Ex. 4 | Rh-Pd-C | 330 | 5.98 | 2.74 | — | 100.0 | 99.0 | 0.4 |
| | " | 330 | 6.22 | 2.58 | — | 100.0 | 98.8 | 0.5 |
| | " | 340 | 5.23 | 2.60 | — | 100.0 | 99.3 | 0.3 |
| Ex. 5 | Rh-C | 330 | 6.21 | 3.14 | — | 99.9 | 98.2 | 1.2 |
| Ex. 6 | Pt-C | 330 | 8.22 | 2.96 | — | 99.8 | 97.8 | 0.8 |
| | " | 340 | 5.55 | 3.12 | — | 100.0 | 98.8 | 0.5 |
| Ex. 7 | Ir-Pd-C | 310 | 4.02 | 2.56 | — | 100.0 | 99.2 | 0.4 |
| | " | 330 | 8.30 | 2.24 | — | 100.0 | 98.5 | 0.3 |
| Comparative Example 3 | Co-Mo-γ-alumina | 330 | 1.20 | — | 9.75 | 76.0 | 76.2 | 3.1 |
| | " | 340 | 1.13 | — | 10.4 | 79.0 | 80.4 | 2.0 |
| Comparative Example 4 | Co-Mo-K-γ-alumi- | 330 | 1.01 | 19.0 | — | 30.3 | 41.3 | 0.5 |
| | " | 340 | 1.21 | 21.2 | — | 37.1 | 41.1 | 0.6 |

EXAMPLE 8

The reaction tube of Example 1 was packed with 15 ml (5.60 g) of 0.01Rh-2Pd-100C obtained by following the same procedure as that of Comparative Example 2. Reduction was effected at 300° C. for 4 hours under conditions of passing through hydrogen. The system was replaced with nitrogen, and then starting material was fed in gas phase at following conditions to conduct the dehydrogenation reaction.

The reaction was continued at the reaction temperature of 300° C. for 42 hours with Steam/4-vinylcyclohexene-1 = 3/1 (mole/mole)
LHSV = 1.09 (ml of liquid 4-vinylcyclohexene-1/ml of catalyst/hr).

The reaction was further conducted for another 2 hours. The reaction product so obtained was analyzed, in consequence of which conversion of 4-vinylcyclohexene-1 was 100 mole%, selectivity to ethylbenzene being 98.4 mole% and selectivity to ethylcyclohexane 1.5 mole%. The reaction was continued for 3 hours by elevating the temperature as high as 330° C., and the reaction was further conducted for another 2 hours. Analyses of the reaction product so obtained showed that conversion of 4-vinylcyclohexene-1 was 100 mole%, selectivity to ethylbenzene being 99.1 mole% and selectivity to ethylcyclohexane 0.9 mole%. Analyses by gas chromatography-mass-spectrometer system of the solution formed at 330° C. showed that minor components other than ethylbenzene and ethylcyclohexane were all identified as minor components in the 4-vinylcyclohexene-1. The amount of hydrogen generated was nearly in agreement with the theoretical amount of it generated.

What we claim is:

1. In a process for preparing corresponding alkyl-substituted aromatic compounds by the gas phase catalytic dehydrogenation of vinylcycloalkenes in contact with a dehydrogenation catalyst supported on a carrier, the improvement comprising said catalytic dehydrogenation being carried out (i) using a dehydrogenation catalyst in which at least one of elements belonging to periods 5 and 6 in the group VIII of the periodic table selected from the group consisting of palladium, rhodium, platinum, iridium and ruthenium is supported on active carbon (ii) by introducing steam into the reaction system,
   (iii) but without introducing hydrogen into the reaction system,
   (iv) at conditions of temperatures ranging from 300° C. to less than 350° C. and pressures less than 2.5 atm (absolute pressure), wherein a liquid hourly space velocity (LHSV) is set at about 5 hr$^{-1}$ or less when the catalytic dehydrogenation is effected in the presence of said catalyst in which palladium alone is supported on active carbon.

2. A process described in the claim 1 in which the dehydrogenation catalyst of (i) above is a catalyst in which a major amount of palladium and a minor amount of at least one of elements selected from the group consisting of rhodium, platinum, iridium and ruthenium are supported on active carbon.

3. A process described in the claim 2 in which the atomic ratio of the major amount of said palladium to the minor amount of said element is 1:0.001 to 1:0.5.

4. A process described in the claim 3 in which said atomic ratio is 1:0.01 to 1:0.1.

5. A process described in the claim 1 in which said vinylcycloalkene is 4-vinylcyclohexene and the corresponding alkyl-substituted aromatic compound is ethylbenzene.

6. The process according to claim 1 wherein the catalytic dehydrogenation is carried out at (iv) a temperature ranging from about 310° C. to about 340° C. and at a pressure ranging from about atmospheric pressure to about 2 atmospheres (absolute pressure).

7. The process according to claim 5 wherein the catalytic dehydrogenation is carried out in the presence of about 20 moles of steam per mole of vinylcycloalkene.

8. The process of claim 6 wherein the catalytic hydrogenation is carried out in the presence of from about 1 to about 10 moles of steam per mole of vinylcycloalkene.

9. The process of claim 2 wherein the catalytic dehydrogenation is carried out at a liquid hourly space velocity of from about 0.1 to about 20 hr$^{-1}$.

10. The process of claim 3 wherein the catalytic dehydrogenation is carried out at a liquid hourly space velocity of from about 0.5 to about 10 hr$^{-1}$.

* * * * *